(12) United States Patent
Arnold et al.

(10) Patent No.: US 10,918,786 B2
(45) Date of Patent: Feb. 16, 2021

(54) METHOD FOR MANUFACTURING A CANNULA UNIT

(71) Applicant: Roche Diabetes Care, Inc., Indianapolis, IN (US)

(72) Inventors: Peter Arnold, Heppenheim (DE); Thomas Kristen, Wald-Michelbach (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

(21) Appl. No.: 16/421,095

(22) Filed: May 23, 2019

(65) Prior Publication Data

US 2019/0275238 A1 Sep. 12, 2019

Related U.S. Application Data

(63) Continuation of application No. PCT/EP2017/080999, filed on Nov. 30, 2017.

(30) Foreign Application Priority Data

Nov. 30, 2016 (EP) ..................................... 16201410

(51) Int. Cl.
*A61M 25/00* (2006.01)
*A61M 5/158* (2006.01)
(Continued)

(52) U.S. Cl.
CPC ........ *A61M 5/158* (2013.01); *A61M 25/0009* (2013.01); *A61M 25/0014* (2013.01);
(Continued)

(58) Field of Classification Search
CPC . A61M 5/158; B29C 45/261; B29K 2221/003
See application file for complete search history.

(56) References Cited

U.S. PATENT DOCUMENTS

| 3,385,553 A * | 5/1968 | Braun ................... B29C 45/261 |
| | | 249/142 |
| 2005/0033237 A1 * | 2/2005 | Fentress ............ A61M 25/0014 |
| | | 604/165.03 |

(Continued)

FOREIGN PATENT DOCUMENTS

| EP | 0 824 930 A2 | 2/1998 |
| EP | 1 504 870 A2 | 2/2005 |

(Continued)

OTHER PUBLICATIONS

International Seach Report and Written Opinion of the International Searching Authority, PCT/EP2017/080999, dated Mar. 12, 2018, 8 pages.

*Primary Examiner* — Jason L Vaughan
*Assistant Examiner* — Amanda Kreiling
(74) *Attorney, Agent, or Firm* — Bose McKinney & Evans LLP

(57) ABSTRACT

Disclosed is a method for manufacturing a cannula unit with a cannula housing and a cannula, in which a cannula is injection molded onto a molding core pin having an outer diameter d1 to produce a cannula having a distal end with a larger outer diameter than the outer diameter of the remaining cannula, a first distal section adjoining the distal end, a second proximal section adjoining the first distal section, and a proximal end. A cannula housing is injection molded onto the distal end and the first distal section of the cannula and the molding core pin is removed from the cannula. A piercing needle with an outer diameter d4 is threaded into the cannula, wherein the diameter d4 of the piercing needle is chosen such that it is smaller than the diameter d1 of the molding core pin.

13 Claims, 6 Drawing Sheets

(51) Int. Cl.
*B29C 45/26* (2006.01)
*A61B 17/00* (2006.01)
*B29C 45/14* (2006.01)
*B29K 221/00* (2006.01)
*B29L 31/00* (2006.01)
*B29C 45/16* (2006.01)

(52) U.S. Cl.
CPC .. *B29C 45/261* (2013.01); *A61B 2017/00526* (2013.01); *A61M 2005/1585* (2013.01); *B29C 45/14* (2013.01); *B29C 45/16* (2013.01); *B29K 2221/003* (2013.01); *B29L 2031/7544* (2013.01); *B29L 2031/7548* (2013.01)

(56) References Cited

U.S. PATENT DOCUMENTS

| | | |
|---|---|---|
| 2008/0228144 A1 | 9/2008 | Liniger et al. |
| 2012/0296290 A1 | 11/2012 | Argauer et al. |
| 2013/0090605 A1 | 4/2013 | O'Connor et al. |
| 2014/0046272 A1* | 2/2014 | Erskine ............ A61M 25/0009 604/263 |

FOREIGN PATENT DOCUMENTS

| | | |
|---|---|---|
| EP | 3 290 073 A1 | 3/2018 |
| WO | WO 02/07804 A1 | 1/2002 |
| WO | WO 2005/046959 A1 | 5/2005 |
| WO | WO 2007/056504 A1 | 5/2007 |
| WO | WO 2012/141760 A1 | 10/2012 |
| WO | WO 2014/105661 A1 | 7/2014 |

\* cited by examiner

METHOD FOR MANUFACTURING A CANNULA UNIT

RELATED APPLICATIONS

This application is a continuation of PCT/EP2017/080999, filed Nov. 30, 2017, which claims priority to EP 16 201 410.4, filed Nov. 30, 2016, the entire disclosures of each of which are hereby incorporated herein by reference.

BACKGROUND

This disclosure relates to methods for manufacturing cannula units for infusion site interfaces and infusion pumps.

Infusion pumps are used for parenterally providing patients with liquid medicaments over longer time periods. Nowadays, infusion pumps with very small dimensions are available that can be carried by the patient on the body. Such small-sized ambulatory infusion pumps are particularly useful for metering small doses of highly effective liquid medicaments, such as insulin for the treatment of diabetes, or analgesics for pain therapy, which are conveyed through a cannula into the tissue of a patient. The treatment of diabetes for example comprises the repeated metering of small doses in the range of nanoliters.

In one approach, an infusion pump, carried somewhere on the body, e.g., attached to a belt, is fluidly connected via flexible tubing to an infusion site interface, also called insertion head, that is attached to the body of the patient. The infusion site interface comprises a cannula unit with a cannula to be inserted into the body tissue, a housing to which the cannula is mounted, and connector means for fluidly connecting the cannula with the flexible tubing connected to the upstream infusion pump. The tubing can be repeatedly connected and disconnected from the infusion site interface. The connector means may for example comprise a septum sealingly closing the fluid system of cannula and housing. The septum can be penetrated by a hollow connector needle, for reversibly establishing a fluid connection. The cannula can be realized as a rigid or semi-rigid cannula with a pointed end that is stiff enough for being inserted into the body tissue on its own, similar to an injection needle. Alternatively, the cannula may be made of a flexible material. Such flexible cannulas are more comfortable during use. Since flexible cannulas cannot be inserted directly into the tissue, an additional piercing device, e.g., in the form of a rigid piercing needle made from metal, e.g., is arranged inside the flexible cannula. A pointed end of the piercing device protrudes from the proximal end of the cannula, the cannula that will be open toward the interstitial fluid. After inserting the piercing device and the stabilized cannula into the body tissue, the piercing device is removed from the cannula. The cannula is now flexible, and remains in the body tissue. Generally, a piercing needle is arranged in such a way that it penetrates a septum, which after withdrawal of the piercing needle sealingly closes the distal end of the now open cannula fluid path. Examples of such infusion site interfaces and insertion heads are shown in WO 02/07804 A1, U.S. Publication No. 2008/0228144 A1, and U.S. Publication No. 2012/0296290 A1.

In another approach, the infusion pump device is directly fluidly connected with the infusion site interface (so called patch pumps). Examples of such embodiments are shown in WO 2007/056504 A1. The infusion site interface may comprise a base plate adhesively connected to the body surface of the patient. The infusion pump unit is then mounted the base plate, for example with a suitable locking mechanism. The fluid connection between infusion pump and cannula is established by a hollow connector needle of the pump, reversibly penetrating a septum of the cannula unit that sealingly closes the distal end of the cannula fluid path. Advantageously, the pump can be repeatedly connected and disconnected from the infusion site interface.

A method for manufacturing flexible cannulas for infusion site interfaces by injection molding is known from WO 2005/046959 A1. The cannula is formed on a core, which is removed when the cannula has sufficiently cured in the molding tool. After completion of the curing, the now hollow flexible cannula is removed from the tool.

WO 2012/141760 A1 discloses a cannula housing with cannula manufactured as one single piece by a single-shot injection molding process. The corresponding tooling is complicated, and compromises must be made regarding the material of the cannula housing and the cannula, which must be identical.

For simplifying the handling of the flexible cannula during the subsequent manufacturing process for the production of infusion site interfaces with flexible cannulas, in a next step a stabilizing pin is introduced into the flexible cannula. This temporary structural unit is then inserted into a previously manufactured housing, and the flexible cannula and the housing are permanently connected, for example by a thermal process. The stabilizing pin is drawn out of the flexible cannula, and is replaced by the actual piercing device.

In the known manufacturing methods for cannula units, a considerable number of elaborate manufacturing steps are involved, for example injection molding in very small dimensions and with very small dimensional tolerances. Due to the accumulation of possible deviations from nominal values during the manufacturing steps of the various elements, as well as during the assembly steps, there is a considerably high rejection rate, in order to avoid any risk of malfunction of the manufactured devices, e.g., leakage.

In order to simplify the manufacturing process and to reduce the rejection rates during manufacturing, U.S. Publication No. 2012/0296290 A1 discloses an advantageous alternative manufacturing method for cannula units with flexible cannulas. A flexible cannula is threaded onto the piercing needle instead of a temporary stabilizing pin. In one embodiment, the distal end of the cannula has a diameter that increases towards the end, compared to the constant diameter of the rest of the cannula. The housing is injection molded around the distal end of the cannula, and the directly adjacent piercing needle. As a result, the cannula is form-locked inside the housing body. When the piercing needle is drawn out of the cannula, a channel is formed in the housing body that continues the cannula fluid channel toward a fluid chamber of the housing.

While such a cannula unit has many advantages, the necessary injection molding process is demanding and requires special tooling. Furthermore, the flexible cannula located inside the polymer matrix of the cannula housing will be compressed to a certain extent during manufacture, due to the high pressures involved in the injection molding step, and essentially remains in this state after manufacture. The compressed cannula wall exerts a force directed radially inwards onto the piercing needle, and on a microscopic scale there may even be a form fit between wall and needle surface. At the same time, since in the injection molding process the hot melted polymer is pressed onto the surface of the metal piercing needle under high pressure, a very close direct contact between the polymer matrix of the cannula housing and the piercing needle results in the section between the distal end of the flexible cannula and the fluid chamber.

The above-mentioned effects lead to a considerable while undefined increase of the static and dynamic friction force between the flexible cannula and the housing on one side, and the piercing needle on the other side. Thus, after insertion of the stabilized cannula into the body tissue, considerably high forces need to be overcome for withdrawing the piercing needle. This can be problematic for the correct and safe handling of insertion site interfaces in which the piercing needle is removed manually.

Furthermore, a too high friction between cannula wall and piercing needle may cause crumpling or even rupture of the flexible cannula during the withdrawal of the piercing needle. Another problem can be caused by an incomplete separation of the polymer material of the cannula unit body and the piercing needle during withdrawal, when the acting high shear forces cause the polymer material adhering to the needle surface to break away from the cannula unit, instead of separating polymer matrix and needle. On one hand such events may cause small polymer particles that could enter the fluid system. Said chips of polymer material may occlude the cannula passageway, or may be conveyed into the tissue of the patient, both of which are unacceptable. On the other hand, during the withdrawal of the piercing needle through the sealing septum, the polymer material still adhering on the needle surface may damage the septum, thereby potentially causing critical leakage of the overall fluid system, which is particularly problematic for insulin infusion pump systems, where an undetected reduced dosing of the highly potent liquid insulin may be hazardous for the patient.

To reduce the high friction forces, the piercing needle can be pre-separated from the housing body material during manufacturing, by turning and/or pulling the piercing needle in a further step subsequent to the injection molding. However, this additional loosening step requires a considerable technical effort, and must be properly controlled and monitored. Furthermore, the problems mentioned above such as cannula crumpling and shear fracture of the polymer material close to the needle surface will also occur in such an automated loosening step, which requires extensive process validation and monitoring of product quality.

There is thus an ongoing need for improvement in the field of cannula units for infusion site interfaces and infusion pumps, and corresponding manufacturing methods.

SUMMARY

This disclosure provides manufacturing methods for cannula units for infusion site interfaces and ambulatory infusion pumps, which overcome one or more of the above-mentioned problems and other problems.

This disclosure also provides a manufacturing method with reduced manufacturing costs, particularly decreased expenditures for tooling and facilities.

This disclosure also provides an increase in the reliability of a manufacturing process for cannula units, and to provide methods for cost-efficiently manufacturing cannula units of high quality.

In an embodiment, a method for manufacturing a cannula unit with a cannula housing and a cannula, comprises the step of injection molding of a cannula onto a molding core pin with an outer diameter $d1$, wherein the cannula has a distal end with an outer diameter that is larger than the outer diameter of the remaining cannula, a first distal section adjoining the distal end, a second proximal section adjoining the first distal section, and a proximal end.

The method further comprises the steps of injection molding of a cannula housing onto the distal end and the first distal section of the cannula, removing the molding core pin from the cannula, and threading a piercing needle with an outer diameter $d4$ into the cannula, wherein the diameter $d4$ of the piercing needle is chosen such that it is smaller than the diameter $d1$ of the molding core pin.

In an embodiment, the clearance between the smallest inner diameter $d2$ of the cannula lumen and the diameter $d4$ of the piercing needle is between 0.02 mm and 0.07 mm.

In an embodiment, the diameter $d4$ of the piercing needle is smaller or equal the smallest inner diameter $d3$ of the cannula lumen in the second proximal section of the cannula located outside of the housing body.

In an embodiment, the diameter $d4$ of the piercing needle is smaller or equal the smallest inner diameter $d2$ of the cannula lumen in the first distal section of the cannula located inside of the housing body.

In an embodiment, the diameter $d4$ of the piercing needle is chosen such that the force resulting from friction between cannula wall and piercing needle surface, which is needed for withdrawing the piercing needle from the cannula at room temperature is less than 0.2N.

In an embodiment, the cannula and the cannula housing are made from different materials.

In an embodiment, the housing body of the cannula housing provides a fluid chamber that is in fluid connection with a cannula lumen of the cannula when the piercing needle is removed.

In an embodiment, the housing body provides a septum seat adjoining to the end of the fluid chamber opposite to the cannula.

In an embodiment, the fluid chamber and the cannula lumen are fluidly connected by a fluid channel formed in the housing body by a section of the molding core pin that is not covered by cannula during the injection molding of the cannula housing.

In an embodiment, a septum is mounted in a septum seat of the cannula housing.

In an embodiment, the septum is mounted in the septum seat before threading the piercing needle into the cannula. The septum is penetrated by the piercing needle when subsequently the piercing needle is threaded into the cannula.

In an embodiment, the septum is mounted in the septum seat after threading the piercing needle into the cannula. The septum is penetrated by the piercing needle when subsequently the septum is mounted in the septum seat.

In an embodiment, the septum is provided already penetrated by the piercing needle. Here, the step of mounting the septum in the septum seat and the step of threading the piercing needle into the cannula can be carried out simultaneously.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure. Components that are identical, or that are identical at least in terms of their function, are designated below by similar reference numbers, e.g., 2, 102; 32, 132.

For the purpose of the present description, the terms "distal" and "proximal" are used to indicate the position of an element in regard to a hypothetical body of a patient when a cannula unit is used for its intended purpose, where the section of the cannula outside of the cannula housing is located inside the body tissue of the patient, and a proximal opening at the tip of the cannula establishes a fluid connection between the fluid system of the cannula unit and the body tissue.

In a first step of a manufacturing method according to the disclosure, a cannula 3 is injection molded onto a cylindrical molding core pin 4 with a certain diameter d1. Corresponding technologies are known to a skilled person, for example from WO 2005/046959 A1, the entire disclosure of which is incorporated herein by reference. The cannula, which is advantageously flexible, can be made from a suitable polymer material for corresponding medical appliances, such as polytetrafluoroethylene (PTFE), linear low-density polyethylene (LLDPE), low density polyethylene (LDPE), high density polyethylene (HDPE), or the like.

Figure 1:
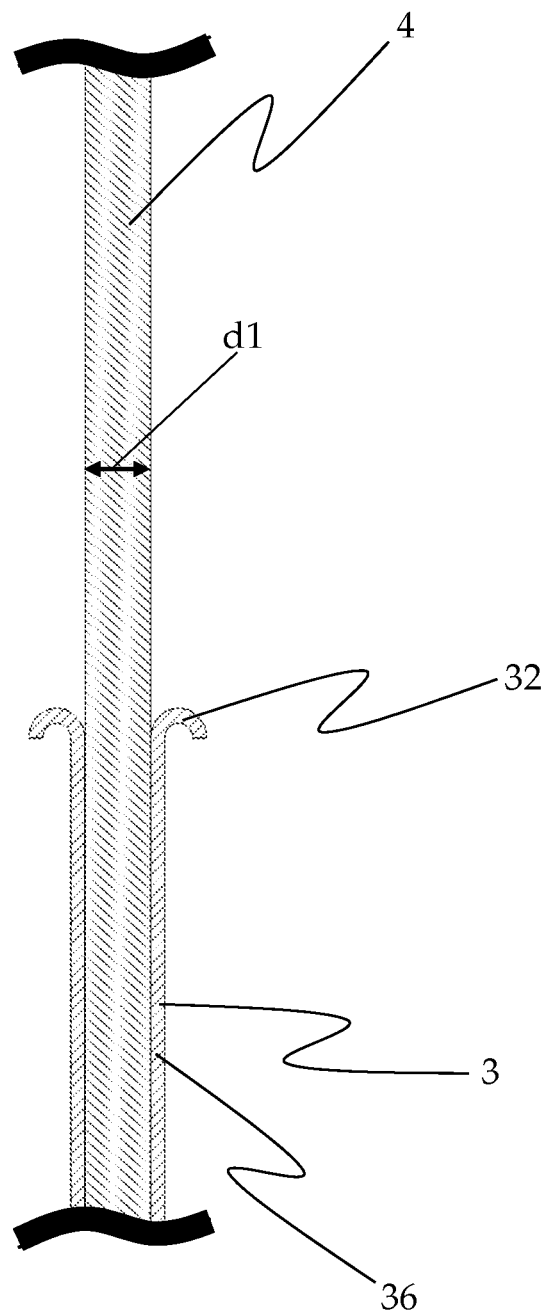
FIG. 1 schematically shows a longitudinal section of a cannula that has been injection molded onto a molding core pin.

For the purpose of the manufacturing method as disclosed herein, the cannula 3 is removed from the mold together with the molding core pin 4. The resulting temporary structure 3, 4 is shown in FIG. 1. The middle section of the molding core pin is shown, with a distal end of the cannula. This combined structure 3, 4 can be handled by holding the molding core pin.

The cannula 3 comprises a distal end 32 with an outer diameter that is larger than the remaining cylindrical cannula wall 36. It has a shape that allows a secure and irreversible mounting of the cannula in the housing body 21, once the housing body is molded around the distal end 32 of cannula 3.

In a next step, the temporary structure 3, 4 is inserted into a suitable injection molding tool, and a housing body 21 of a cannula housing 2 is injection molded around a distal end 32 and a first distal section 34 of the cannula 3. The housing body 21 is advantageously made from a suitable polymer material for medical appliances, advantageously a thermoplastic polymer, such as e.g., methyl methacrylate acrylonitrile-butadiene-styrene (MABS), polycarbonate (PC), polymethylmethacrylate (PMMA), polypropylene (PP), polyethylene (PE) and the like.

During the injection molding process, the applied very high pressure in the mold is directly transferred by the fluid melted polymer onto the cannula wall 36 located inside the mold cavity, which defines the first, distal section 34 of the cannula 3. This leads to a radial compression of the cannula wall 36 in this section 34 toward the center of the molding core pin 4. The resulting radial bias of the cannula wall 36 in section 34 remains after cooling down and solidification of the housing body 21.

Figure 2:
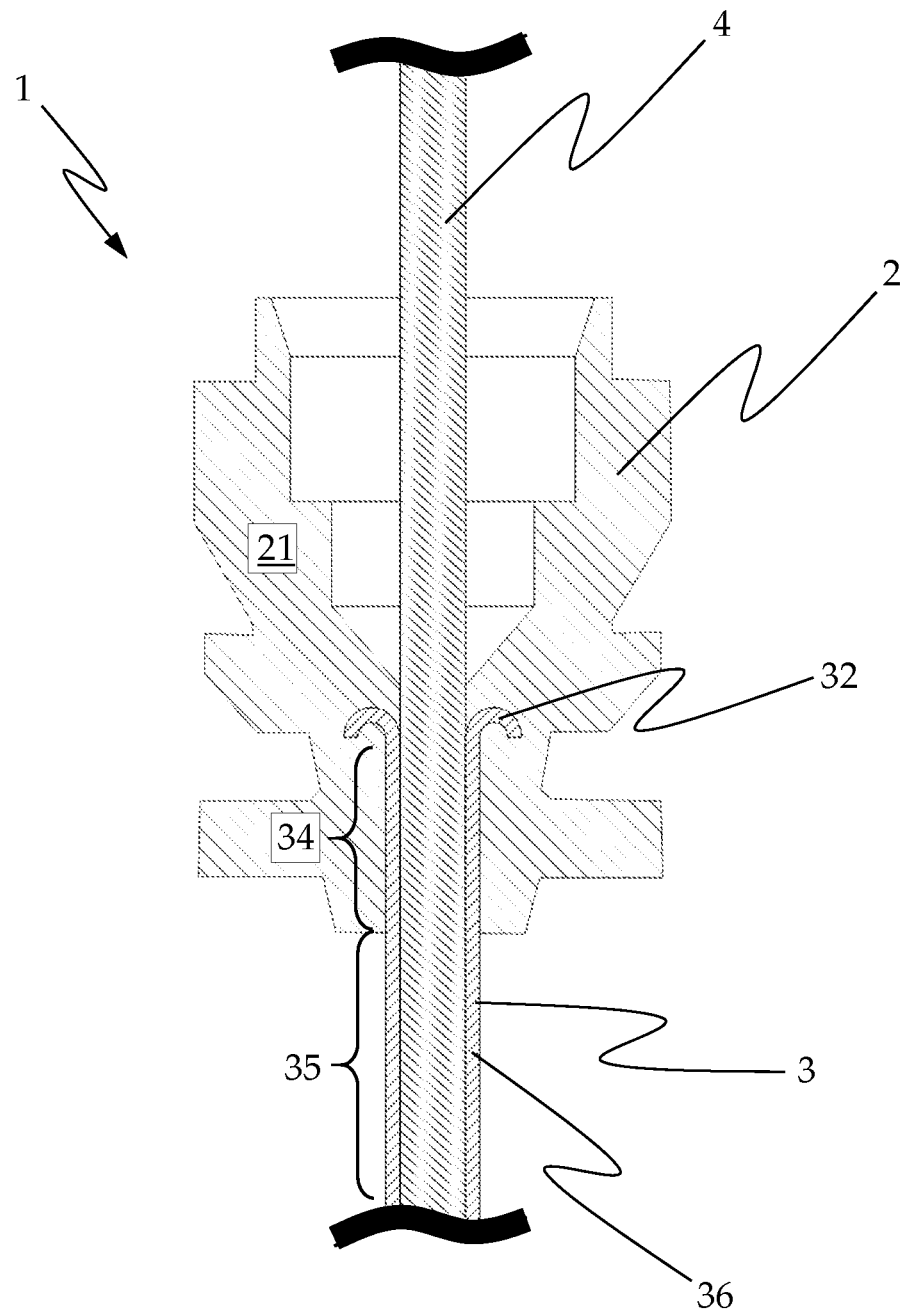
FIG. 2 schematically shows a longitudinal section of a cannula unit after injection molding the cannula unit around the distal end of the cannula from FIG. 1.

The resulting temporary structure 2, 3, 4 comprising cannula unit 1 with cannula housing 2 and cannula 3, and molding core pin 4, after removal from the molding tool (not shown) is depicted in FIG. 2. In a next step, the molding core pin 4 is removed, arriving at the intermediate product shown in FIG. 3.

Figure 3:
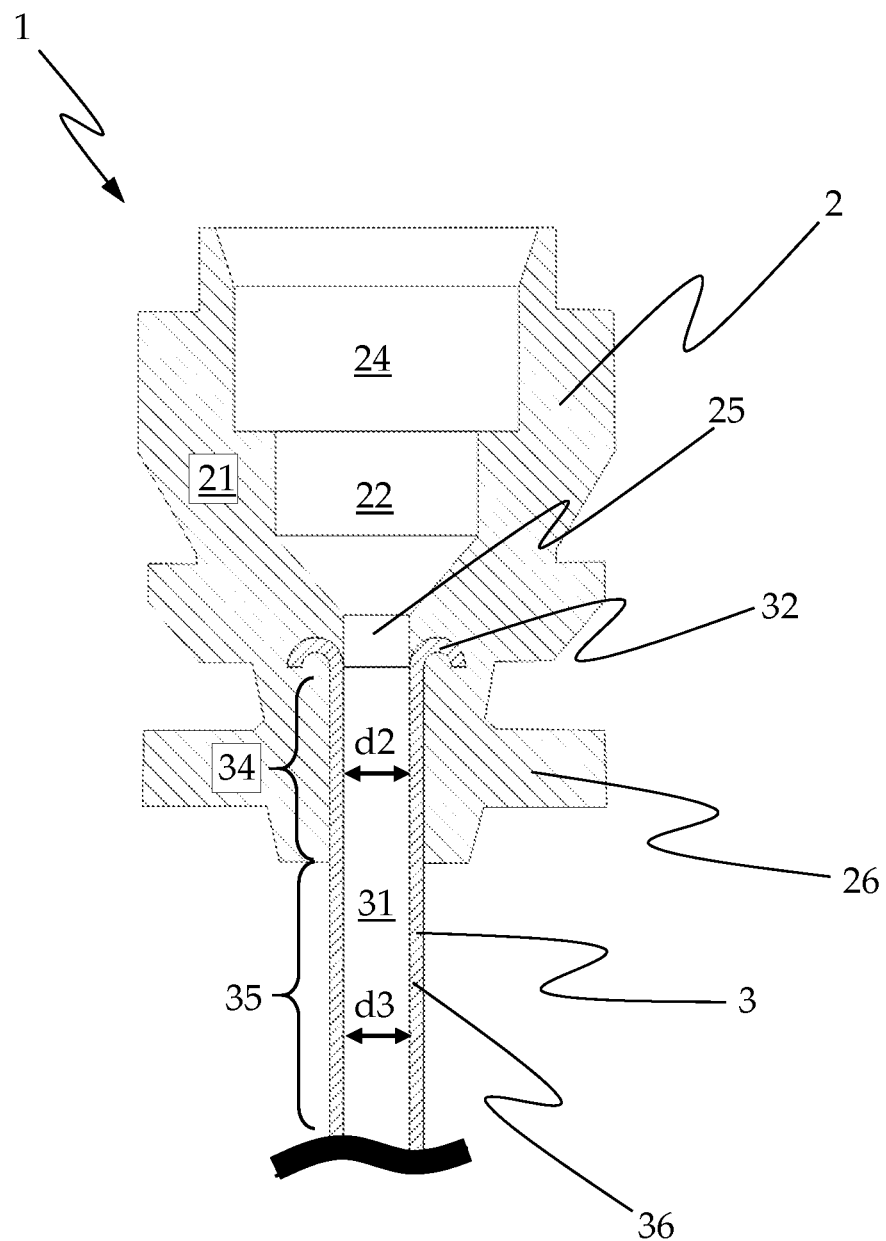
FIG. 3 schematically shows a longitudinal section of the cannula unit of FIG. 2, after removal of the cannula molding pin.

It should be noted that, alternatively, it is possible to remove the molding core pin while the cannula unit is still in the molding tool, before subsequently demolding the cannula unit from the molding tool and arriving at the cannula unit in FIG. 3. However, temporarily leaving the molding core pin in the cannula unit simplifies the handling of the demolded cannula unit, particularly the transfer to the next tool in the production process, by holding and moving the molding core pin.

The outer shape of the cannula housing 2 depends on the future use of the cannula unit, particularly on how it is intended to be mounted in a larger structure, e.g., of an infusion set interface or a patch pump unit. On a distal end of a housing body 21 of the cannula housing 2, a septum seat 24 is provided, in which in a later step a septum can be mounted. A fluid chamber 22 is located below the septum seat 24, the fluid chamber 22 opening toward a fluid channel 25. Said fluid channel 25 has been formed in the housing body by a short section of the molding core pin 4, located inside the molding cavity of the molding tool. The inner diameter of the fluid channel 25 is equal to the outer diameter d1 of the molding core pin 4. The fluid channel 25 directly passes over into the cannula lumen 31, in the area where the distal end 32 of cannula 3 is embedded in the polymer matrix of housing body 21. The positively locked distal end 32 of the cannula ensures a safe and irreversible connection between cannula 3 and cannula housing 2. In addition a sealingly tight connection between the inner fluid system 22, 25 of the cannula housing 2 and the fluid system 31 of the cannula 3 is achieved. Thus, the fluid chamber 22 is fluidly connected to the opening at the proximal tip of the cannula (not shown).

During the manufacturing steps occurred so far, certain geometric parameters of the cannula unit inevitably change, and must be taken into account. After injection molding of the cannula 3 around molding core pin 4, the inner diameter of the cannula is identical to the outer diameter d1 of the molding core pin 4. However, during the further cooling-down after demolding, the polymer material of the cannula shrinks more than the steel of the molding core pin, resulting in a certain strain of the cannula threaded on the molding core pin. After removal of the molding core pin from cannula 3 and housing body 21, the strain on the cannula wall is released and the cannula shrinks to a certain extent. The resulting inner diameter d3 of the cannula lumen 31 is smaller than the outer diameter d1 of the molding core pin 4.

In the first distal section 34 of the cannula 3 located inside the housing body, the cannula wall 36 has been additionally radially biased during the injection molding of the cannula housing, as explained further above. As a result, after removal of the molding core pin, the cannula wall in this section 34 radially expands inwards to a certain extent, further decreasing the inner diameter of the cannula 3. The smallest inner diameter d2 of the cannula lumen 31 in the first distal section 34 is thus smaller than the inner diameter d3 of the cannula lumen 31 in the second proximal section 35 of the cannula 3, which has not been subjected to the injection mold pressure.

Figure 4:
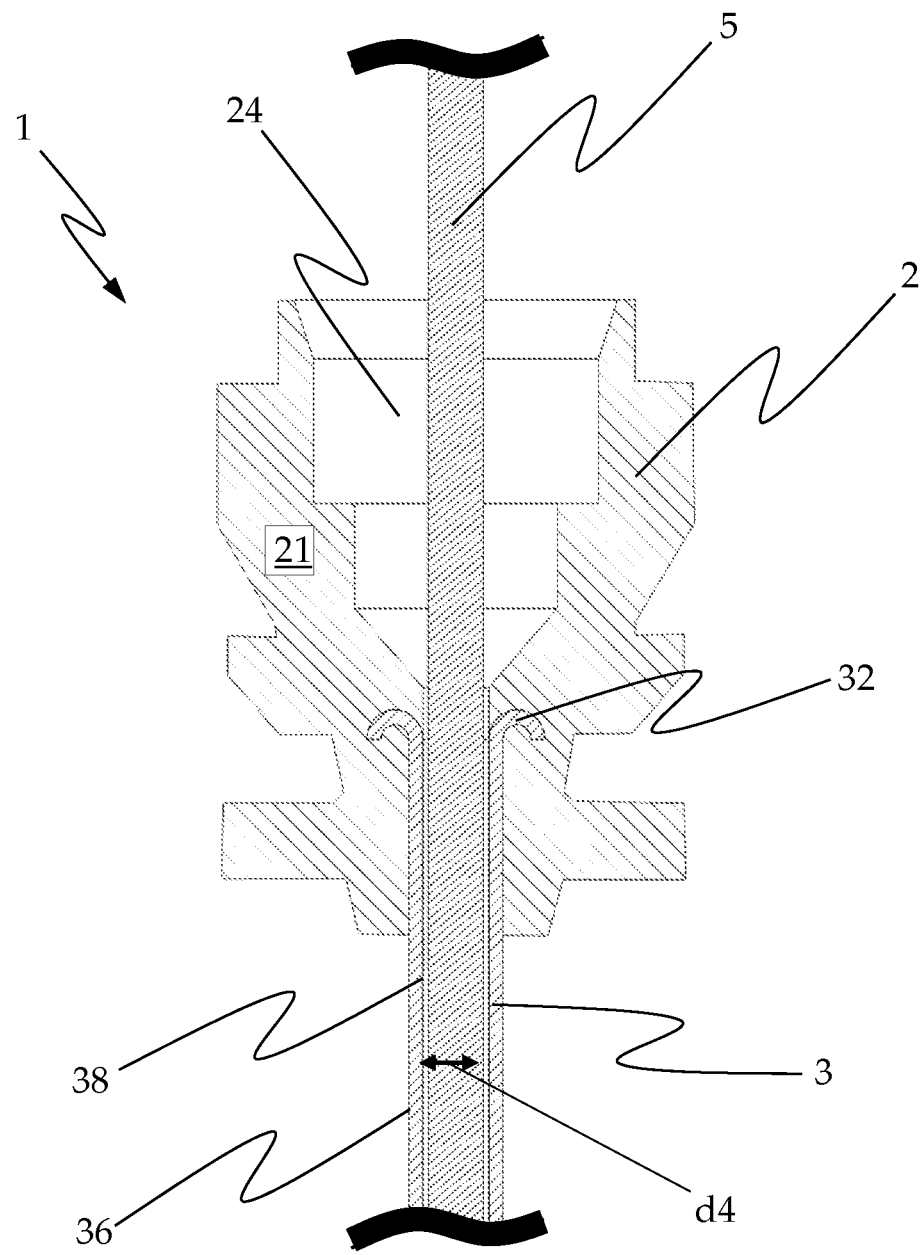
FIG. 4 schematically shows a longitudinal section of the cannula unit of FIG. 3, after threading of the piercing needle into the cannula.

In the next manufacturing step, a pointed piercing needle 5 is threaded into the cannula 3, arriving at the phase shown in FIG. 4. The outer diameter d4 of the piercing needle 5 is chosen smaller than the diameter d1 of the molding core pin. Advantageously, the diameter d4 is smaller or equal to the inner diameter d3 of the cannula 3 in the second proximal section 35, resulting in a small gap 38 between cannula wall 36 and piercing needle 5. In case d4 is equal to d3, the gap is essentially zero. Nevertheless there is no form lock or bias force acting on the cannula and piercing needle. This allows setting a well-defined static and sliding friction force between the cannula wall and piercing needle. The sliding friction should be low enough to allow a simple insertion of the piercing needle into the cannula. The static and sliding friction should be as small as possible, in order to avoid a user having to exert a too high of a force when later withdrawing the piercing needle, and to avoid the cannula wall wrinkling during withdrawal of the piercing needle. At the same time, static friction should be high enough to avoid wrinkling of the cannula during insertion of the stabilized cannula into the body tissue of a patient.

If the outer diameter d4 of the piercing needle 5 is larger than the smallest inner diameter d2 of the cannula 3 in the first distal section 34, the threading of the piercing needle 5 into the cannula 3 will expand the inner diameter in this cannula section 34, thereby increasing static and sliding friction. If the outer diameter d4 of the piercing needle 5 is smaller or equal to the smallest inner diameter d2 of the cannula 3 in the first distal section 34, the inner diameter in this cannula section 34 will remain unchanged.

In a typical specific example, the outer diameter d4 may, e. g, be 0.4 mm with a tolerance of −0.01 mm. The smallest inner diameter d2 of the cannula 3 may, e.g., 0.44 mm with a tolerance of +/−0.02 mm. The clearance d2-d4 between the piercing needle 5 and the cannula 3 may, e.g., be in a rage of minimum 0.02 mm and maximum 0.07 mm.

A skilled person will choose the appropriate diameter d4 of the piercing needle, depending on the concrete parameters of the cannula housing and the manufacturing process, with the aim of fulfilling the above-mentioned criteria and achieving a withdrawal force that reliably lies within a certain range.

For a manufacturing process in accordance with this disclosure, a withdrawal force close to zero may be achieved, below a limit of measurement, as compared to a withdrawal force in a range of, e.g., 8 N to 12 N otherwise.

Figure 5:
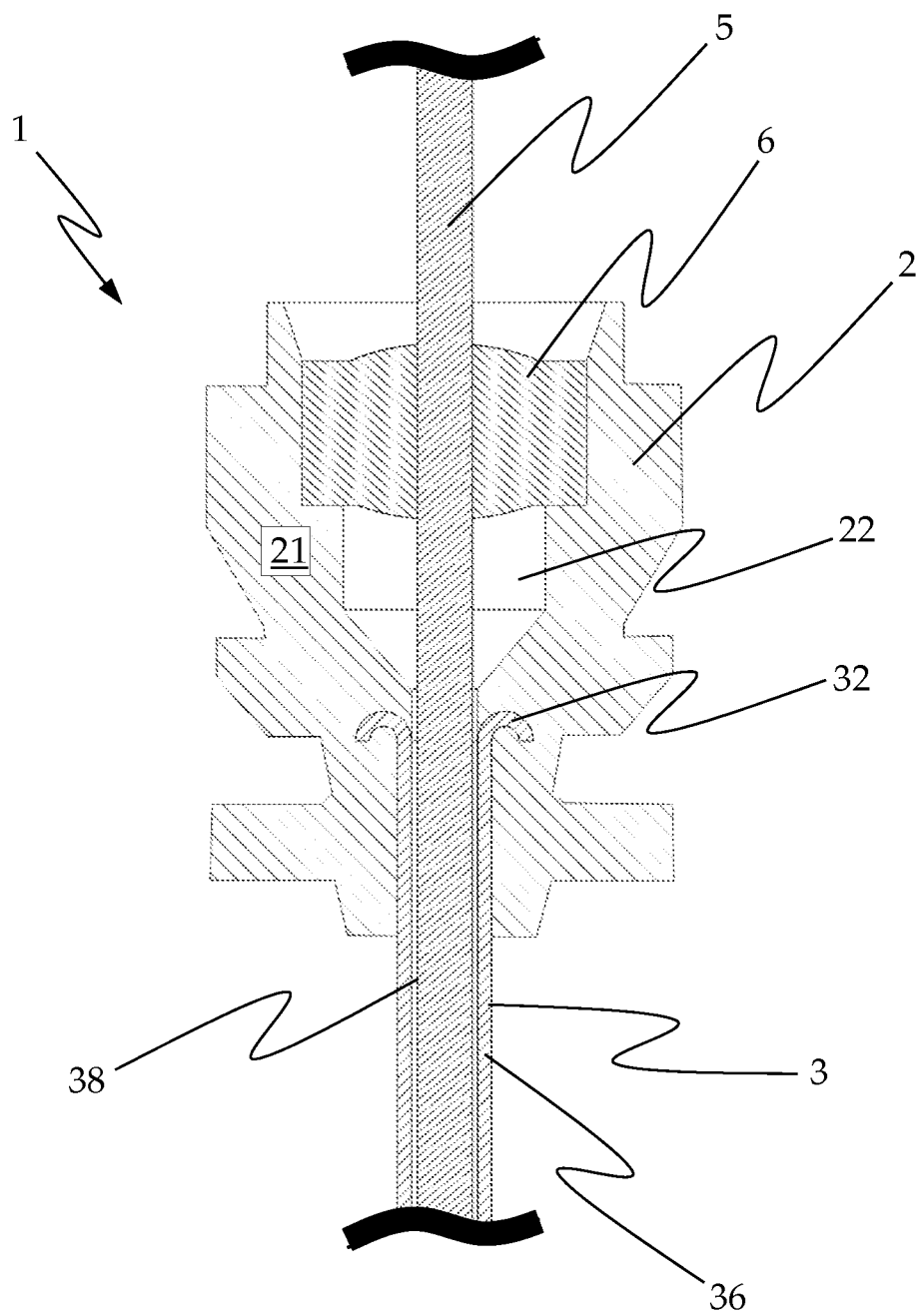
FIG. 5 schematically shows a longitudinal section of the cannula unit of FIG. 4, after mounting a septum into the septum seat.

For mounting the septum 6, the piercing needle 5 inevitably has to penetrate the septum 6 at some stage in the manufacturing process. One possibility is to insert the septum when the piercing needle is already in place, sliding the already penetrated septum over the piercing needle from a distal end of the needle, until it is finally mounted in the septum seat. One arrives at the situation shown in FIG. 5, where the mounted septum 6 sealingly closes the distal end of the fluid chamber 22. When during the intended use of the cannula unit the piercing needle is withdrawn, the elastic septum will keep the fluid system sealingly closed. Depending on the intended use, the septum may also be used for releasably connecting an outer fluid system of a pump system to the cannula unit via a hollow connector needle.

In another variant of the disclosed manufacturing method, the septum 6 may be mounted in the septum seat 24 prior to the insertion of the piercing needle 5 into the cannula 3. In this case, the pointed piercing needle will penetrate the septum during the threading step.

In yet another variant, the piercing needle and the septum can be provided in a state where the piercing needle has already penetrated the septum. The septum then can be set into place before, during, or after the threading process of the piercing needle and cannula.

Figure 6:
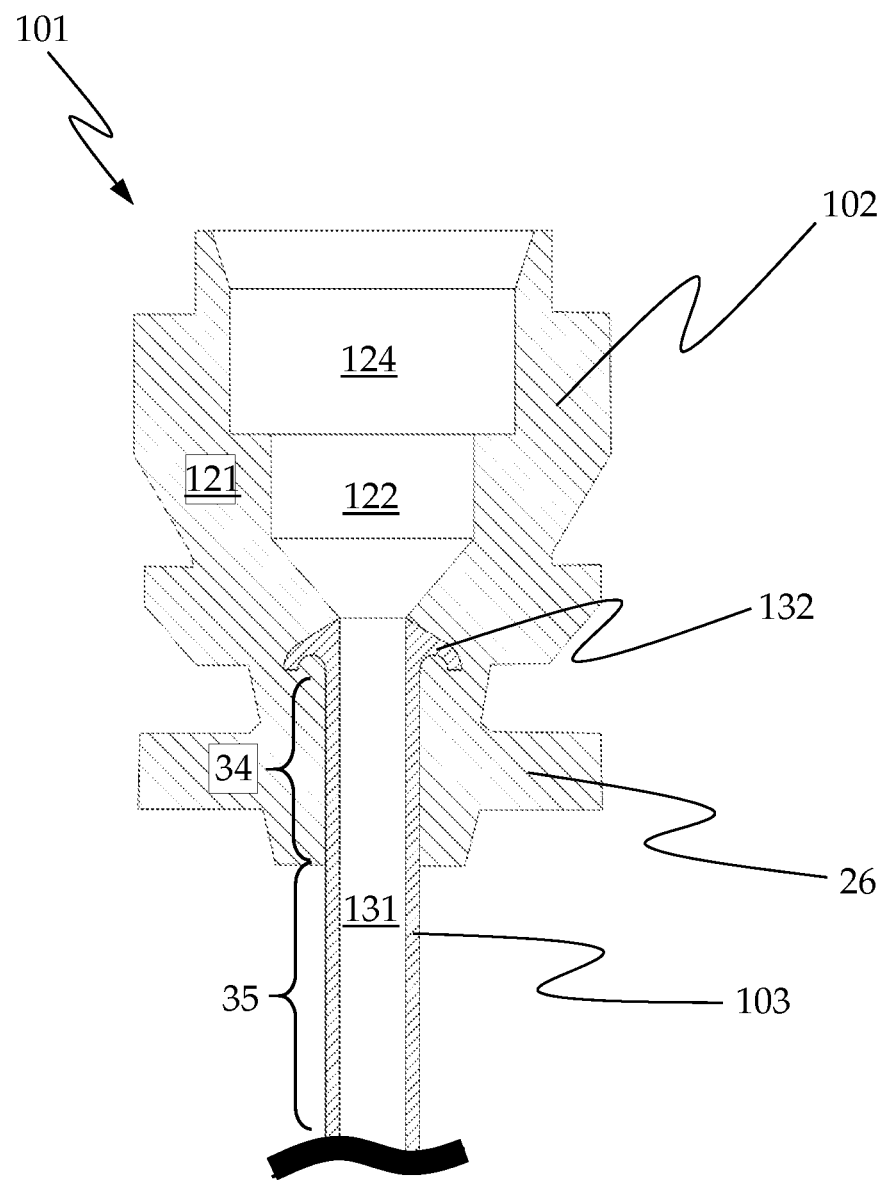
FIG. 6 schematically shows a longitudinal section of another embodiment of a cannula unit, at the same stage of the manufacturing process as shown in FIG. 3.

In a further advantageous variant of the disclosed manufacturing method, the geometry of the cannula 103 and the cannula housing 102 are chosen such that no fluid channel is formed in the housing body 121. A possible embodiment of a cannula unit 101 resulting from such method is shown in FIG. 6, in the same phase of the manufacturing process as shown in FIG. 3. The opening at the distal end 132 of the cannula 103 directly opens toward the fluid chamber 122.

The manufacturing methods for cannula units as discussed so far can be adapted by a skilled person for the manufacturing of more complex cannula unit structures.

The cannula units produced by the manufacturing methods as discussed so far have been equipped with only one septum, which can be used both for withdrawing the piercing needle, and for establishing a fluid connection with an infusion pump, using a hollow connector needle. However, cannula units manufactured by the method according to this disclosure can also be equipped with a separate connection element for connecting the cannula unit to an upstream infusion pump. For example can the cannula unit be provided with a further connector port with septum, which is fluidly connected to the fluid chamber by a fluid channel provided in the housing body. Examples of such cannula units are disclosed e.g., in FIG. 1B of U.S. Publication No. 2012/0296290 A1, and in FIG. 21 of U.S. Publication No. 2008/0228144 A1, the entire disclosures of which are hereby incorporated herein by reference. The manufacturing method according to this disclosure can be straightforwardly integrated into the manufacturing of such cannula units.

The method according to this disclosure can also be applied in the manufacturing process of cannula units as disclosed in European Patent Application No. 16186167.9 filed by the Applicants, having the title "CONNECTOR DEVICE," filed on Aug. 29, 2016, the entire disclosure of which is hereby incorporated herein by reference. Said application discloses a connector device comprising two connector parts for reversibly establishing a fluid connection without the need for a hollow connector needle. Said connector parts can be combined with a cannula unit with septum and piercing needle, for example in an infusion site interface, wherein the connector part allows to fluidly connect the cannula unit with an infusion pump unit via the separate connector device. The manufacturing method according to this disclosure can be straightforwardly integrated into the manufacturing of such complex devices.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERALS 1 cannula unit
2 cannula housing
21 housing body
22 fluid chamber
24 septum seat
25 fluid channel
26 retention flange
3 cannula
31 cannula lumen
32 distal end of cannula
34 first distal section of cannula
35 second proximal section of cannula
36 cannula wall
38 gap
4 molding core pin
5 piercing needle, insertion pin
6 septum
101 cannula unit
102 cannula housing
121 housing body
122 fluid chamber
124 septum seat
103 cannula
131 cannula lumen
132 distal end of cannula
134 first distal section of cannula
135 second proximal section of cannula
d1 outer diameter of molding core pin
d2 smallest inner diameter of cannula lumen in a first distal section of cannula
d3 largest inner diameter of cannula lumen in a second proximal section of cannula
d4 outer diameter of piercing needle

What is claimed is:

1. A method for manufacturing a cannula assembly, comprising:
    injection molding a cannula onto a molding core pin having an outer diameter d1 to produce a cannula having a distal end with a larger outer diameter than the outer diameter of the remaining cannula, a first distal section adjoining the distal end, a second proximal section adjoining the first distal section, and a proximal end;
    injection molding a cannula housing onto the distal end and the first distal section of the cannula;
    removing the molding core pin from the cannula; and
    threading a piercing needle with an outer diameter d4 into the cannula, wherein the diameter d4 of the piercing needle is chosen such that it is smaller than the diameter d1 of the molding core pin.

2. The method of according to claim 1, wherein the cannula defines a cannula lumen and a clearance between a smallest inner diameter d2 of the cannula lumen and the diameter d4 of the piercing needle is between 0.02 mm and 0.07 mm.

3. The method of according to claim 1, wherein the cannula defines a cannula lumen and the diameter d4 of the piercing needle is smaller than or equal to a smallest inner diameter d3 of the cannula lumen in the second proximal section of the cannula located outside of the housing body.

4. The method of according to claim 1, wherein the cannula defines a cannula lumen and the diameter d4 is smaller than or equal to a smallest inner diameter d2 of the cannula lumen in the first distal section of the cannula located inside of the housing body.

5. The method of according to claim 1, wherein the diameter d4 of the piercing needle is chosen such that the force resulting from friction between cannula wall and piercing needle surface, which is needed for withdrawing the piercing needle from the cannula at room temperature, is less than 0.2N.

6. The method according to claim 1, wherein the cannula and the cannula housing are made from different materials.

7. The method according to claim 1, wherein the housing body of the cannula housing provides a fluid chamber in fluid communication with a cannula lumen of the cannula when the piercing needle is removed.

8. The method according to claim 7, wherein the housing body provides a septum seat adjoining the end of the fluid chamber opposite to the cannula.

9. The method according to claim 7, wherein the fluid chamber and the cannula lumen are fluidly connected by a fluid channel formed in the housing body by a section of the molding core pin not covered by cannula during the injection molding of the cannula housing.

10. The method according to claim 1, comprising mounting a septum in a septum seat of the cannula housing.

11. The method according to claim 10, wherein the septum is mounted in the septum seat before threading the piercing needle into the cannula, whereby the septum is penetrated by the piercing needle when the piercing needle is subsequently threaded into the cannula.

12. The method according to claim 10, wherein the septum is mounted in the septum seat after threading the piercing needle into the cannula, whereby the septum is penetrated by the piercing needle when the septum is subsequently mounted in the septum seat.

13. The method according to claim 10, wherein the septum is provided in a state in which the septum is penetrated by the piercing needle, whereby the step of mounting the septum in the septum seat and the step of threading the piercing needle into the cannula are carried out simultaneously.

* * * * *